United States Patent [19]

D'Silva

[11] 4,369,189
[45] Jan. 18, 1983

[54] NOVEL UNSYMMETRICAL FORMAMIDINE-SULFENYLATED CARBAMATE COMPOUNDS

[75] Inventor: Themistocles D. J. D'Silva, South Charleston, W. Va.

[73] Assignee: Union Carbide Corporation, Danbury, Conn.

[21] Appl. No.: 215,087

[22] Filed: Dec. 10, 1980

[51] Int. Cl.$^3$ .................. A01N 9/12; C07D 307/83
[52] U.S. Cl. ...................... 424/285; 260/544 C; 260/453 RW; 260/465 D; 542/416; 560/15; 560/16; 564/40; 564/47; 424/246; 424/247; 424/248.4; 424/248.5; 424/248.51; 424/270; 424/275; 426/276; 426/277; 426/315; 426/317; 426/319; 426/300; 426/304; 426/322
[58] Field of Search ....... 260/544 C, 453 RW, 465 D, 260/453; 560/15, 16; 564/40, 47; 542/416; 424/246, 247, 248, 248.4, 248.5, 248.51, 270, 275, 276, 277, 315, 317, 319, 300, 304, 278, 285, 322

[56] References Cited

U.S. PATENT DOCUMENTS

| | | | |
|---|---|---|---|
| 3,947,591 | 3/1976 | Rizzo et al. | 424/326 |
| 4,072,750 | 2/1978 | D'Silva | 424/277 |
| 4,081,550 | 3/1978 | D'Silva | 424/277 |
| 4,096,269 | 6/1978 | D'Silva | 560/16 |
| 4,098,902 | 7/1978 | Boger et al. | 424/322 |
| 4,115,583 | 9/1978 | Boger et al. | 424/300 |
| 4,122,204 | 10/1978 | D'Silva | 424/285 |
| 4,124,721 | 11/1978 | D'Silva | 424/285 |
| 4,138,423 | 2/1979 | D'Silva | 560/16 |
| 4,156,731 | 5/1979 | D'Silva | 424/277 |
| 4,166,864 | 9/1979 | D'Silva | 424/277 |
| 4,169,894 | 10/1979 | D'Silva | 424/277 |
| 4,179,514 | 12/1979 | D'Silva | 424/285 |
| 4,232,035 | 11/1980 | D'Silva | 424/270 |

OTHER PUBLICATIONS

Fahmy et al., J. Agr. Food Chem., 22, (1974), pp. 59–62.

*Primary Examiner*—Arthur P. Demers
*Attorney, Agent, or Firm*—William R. Moran

[57] ABSTRACT

Novel unsymmetrical formamidine-sulfenylated carbamate compounds exhibit broad-spectrum insecticidal, miticidal and nematocidal activity.

68 Claims, No Drawings

NOVEL UNSYMMETRICAL FORMAMIDINE-SULFENYLATED CARBAMATE COMPOUNDS

DESCRIPTION OF THE INVENTION

This invention relates to novel broad-spectrum acaricidal, insecticidal and nematocidal compounds. This invention also relates to methods for preparing the novel compounds and to methods and compositions for controlling insects, acarid and nematode pests employing the novel compounds of this invention.

The novel compounds of this invention are compounds of the general formula:

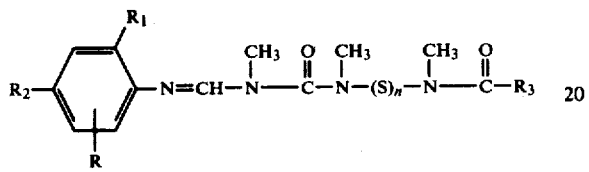

wherein:

n is 1 or 2;

R is hydrogen, halogen or alkyl;

$R_1$ and $R_2$ are individually halogen, alkyl, trihaloalky or di- or trihaloalkoxy; provided that the total number of carbon atoms in any one of R, $R_1$ or $R_2$ should not exceed four;

$R_3$ is:

A. fluorine;

B. a phenoxy group which may be unsubstituted or substituted with one or more alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxycarbonylamino, N,N-dialkyl-formamidino, cyano, dioxolanyl, or dithiolanyl substituents in any combination; provided that the total number of aliphatic carbon atoms in $R_3$ should not exceed twelve;

C. 1-naphthoxy, tetrahydronaphthoxy, dihydrobenzofuranoxy, benzodioxalanoxy, or benzothienoxy, all of which may be unsubstituted or substituted with one or more alkyl groups; provided that the total number of aliphatic carbon atoms in $R_3$ should not exceed twelve;

D. a group of the formula:

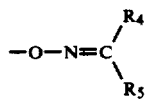

wherein:

$R_4$ is chloro, alkyl, alkylthio, cyanoalkylthio, cyano or hydrogen;

$R_5$ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstituted or substituted with one or more alkyl, chloro or fluoro substituents in any combination; provided that $R_4$ and $R_5$ may not both be hydrogen; and further provided that the total number of aliphatic carbon atoms in $R_4$ and $R_5$ does not exceed twelve; or E. a group of the formula:

wherein:

A is a five- or six-membered divalent aliphatic chain which includes one, two or three divalent oxygen, sulfur, sulfinyl or sulfonyl substituents and which may include not more than one divalent amino, carbonyl or alkylamino moiety in any combination; and which may be unsubstituted or substituted with one or more alkyl substituents; provided that the total number of aliphatic carbon atoms in A should not exceed twenty-four and provided further that when A is substituted with an alkylamino moiety, the total number of carbon atoms in said alkylamino moiety should not exceed eight, and provided further that sulfur may be in any of its oxidation states.

Generally, the preferred compounds of this invention are those wherein:

$R_1$ and $R_2$ are both alkyl;

$R_1$ is alkyl and $R_2$ is halogen;

n is one;

$R_3$ is fluorine, phenoxy substituted with alkyl, alkylthio, alkoxy or dioxolanyl; naphthaloxy, dihydrobenzofuranoxy, benzodioxalonoxy; a group of the formula:

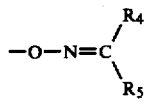

wherein $R_4$ is alkyl and $R_5$ is alkylthio; or a group of the formula:

wherein A is a divalent heterocyclic chain completing a 2-oximino-1,4-dithiane, 2-oximino-1,3-dithiane, 4-oximino-1,3-dithiolane, 2-oximino-1,4-dioxane, 2-oximino-tetrahydro-1,4-thiazin-3-one, 2-oximino-1,3-dithiolane, 2-imino-4-oximino-1,3-dithiolane, 3-oximinothiophane, 2-oximino-thiophane, 2-oximinotetrahydro-1,4-oxathiane, 4-oximino-1,3-oxathiolane, 2-oximino-thiazolidin-3-one, 2-oximino-1,3-thiazolidin-4-one or 2-oximino-tetrahydro-1,4-thiazin-5-one ring structure, wherein sulfur may be in any of its oxidation states.

Activity is greatest in compounds in which $R_1$ and $R_2$ are methyl. Compounds in which $R_1$ is methyl and $R_2$ is halogen are also particularly active. Compounds wherein $R_3$ is dihydrobenzofuranoxy are very active. Also very active are oxime compounds containing a methyl group in the $R_4$ position and a methylthio group in the $R_5$ position.

There are two convenient methods by which the unsymmetrical formamidine-sulfenylated carbamate compounds of this invention can be prepared. The first method consists of two steps. In Step A of Method I, a formamidine compound is reacted with a sulfenylated bis-carbamoyl fluoride to obtain an unsymmetrical fluoro-formamidine-sulfenylated carbamate compound. In Step B of Method I, said unsymmetrical fluoro-formamidine-sulfenylated carbamate is reacted with a naphthol, phenol or oxime to form an unsymmetrical formamidine-sulfenylated carbamate compound. Both Steps are conducted in the presence of an acid acceptor. Method I is illustrated by the following general reaction method, wherein n, R, $R_1$, $R_2$ and $R_3$ are as defined previously:

METHOD I
STEP A

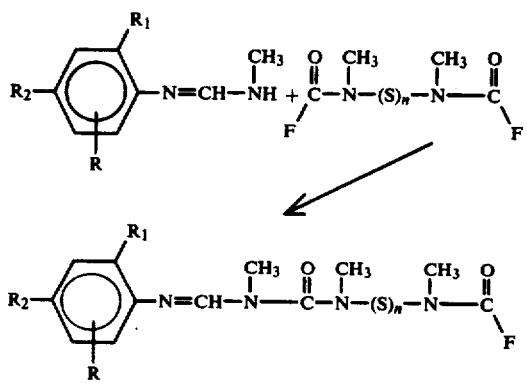

STEP B

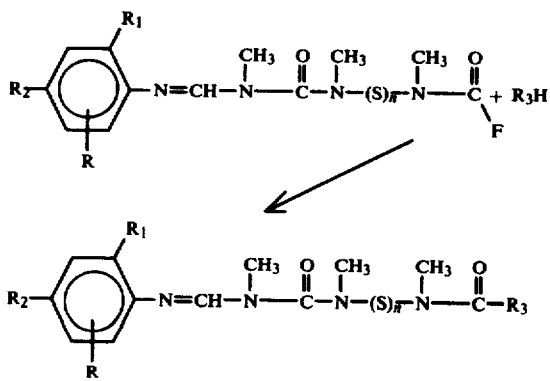

In Method II, a formamidine is reacted with an unsymmetrical sulfenylated carbamoyl fluoride to obtain the unsymmetrical formamidine-sulfenylated carbamate compounds of this invention. Method II is illustrated by the following general reaction method, wherein n, R, $R_1$, $R_2$ and $R_3$ are as defined previously:

METHOD II

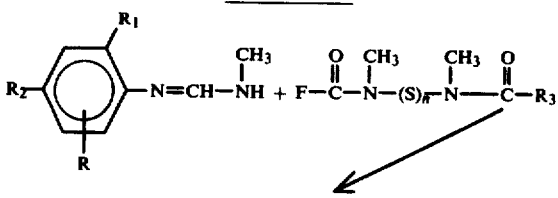

-continued
METHOD II

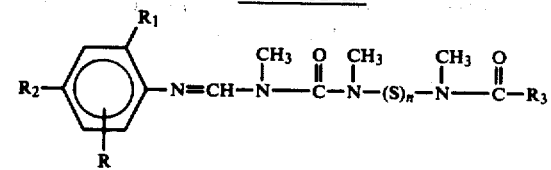

The reactions illustrated above in Methods I and II are conducted in the presence of an acid acceptor. Said acid acceptor may be either an organic or inorganic base. Illustrative of organic bases which may be used are tertiary amines, such as triethylamine, pyridine, ethylmethyl pyridine, quinolines or 1,4-diazabicyclo[2.2.2] octane, and alkali metal alkoxides, such as sodium methoxide, sodium ethoxide and the like. Illustrative of inorganic bases useful in conducting these reactions are sodium carbonate, potassium carbonate, sodium hydroxide and potassium hydroxide. Stoichiometric quantities of the acid acceptor and the reactants are used, although a slight excess of the acid acceptor may be used if desired.

It is preferable to conduct the reactions in the presence of an inert solvent such as acetone, chloroform, toluene, dimethyl formamide or the like. Pyridine may be used as a solvent as well as acid acceptor.

The reaction temperature is not critical and can be varied over a wide range. The reaction is preferably conducted at a temperature of from about $-30°$ C. and upwards to approximately 120° C.

Reaction pressures are not critical. The process can be conducted at either subatmospheric, atmospheric or superatmospheric pressure. For convenience the reaction is usually conducted at atmospheric or autogeneous pressure.

The formamidine reactants used as starting materials in the preparation of the novel unsymmetrical formamidine-sulfenylated carbamates of this invention in Methods I and II can be prepared by those skilled in the art according to methods disclosed in U.S. Pat. No. 3,884,968 and Belgium Pat. No. 767912. An appropriately substituted aniline is reacted with N-methyl-formamide in the presence of a suitable condensing agent to produce an N-methyl-formamidine. The 2,4-dimethylphenylformamidine reactants can also be prepared by reacting methylamine with a dimethylphenylformamidate in the presence of a suitable condensing agent or by reacting methylamine with 2,4-dimethylphenylisocyanide in the presence of a suitable catalyst in accordance with methods disclosed in U.S. Pat. No. 3,884,968.

The sulfenylated carbamoyl fluoride reactants used as starting materials in Method I can be prepared by reacting methyl isocyanate with hydrofluoric acid and further treating the reaction product with sulfur dichloride to produce bis-carbamoyl fluoride reactants.

The disulfide bis-carbamoyl fluoride reactants used as starting materials in Method I can be prepared by reacting 1 mol of N-methyl carbamic acid fluoride with 2 mols. of disulfur dichloride in the presence of an acid acceptor in accordance with the method disclosed in U.S. Pat. No. 3,639,471.

The carbamoyl fluoride compounds used as starting materials in Method II can be prepared in accordance with methods disclosed in German Offen. No. 2,813,374 wherein a sulfenylated bis-carbamoyl fluoride is reacted with an appropriate phenol, naphthol or oxime in the presence of an acid acceptor as illustrated by the following general reaction method:

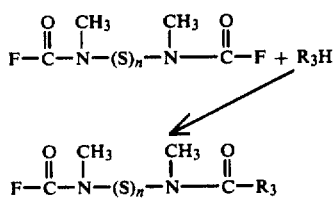

wherein $R_3$ is as defined above but not fluorine.

The following examples are illustrative of the methods of preparing the novel compounds of this invention:

EXAMPLE I

Preparation of 1-Fluoro-7-(2,4-dimethylphenylimino)-2,4,6-triaza-2,4,6-trimethyl-3-thia-1,5-dioxoheptane (Step A, Method I)

To a solution of 38.45 g (0.209 m) of N,N'-bis-(N-methyl-N-fluorocarbonylamino)sulfide in 750 ml of toluene was added a solution of 33.87 g (0.209 m) of N-(2,4-dimethylphenyl)-N'-methylformamidine and 21.15 g (0.209 m) of triethylamine in 250 ml of toluene. The feed was completed in 45 minutes and the reaction mixture was stirred at room temperature for 16 hours. The crude mixture was washed with water, dried and concentrated to afford 62.0 g of an amber-colored viscous oil. The material was purified by low pressure liquid chromatography.

Calc'd for $C_{14}H_{19}FN_4O_2S$: C, 51.22; H, 5.87; N, 17.17; Found: C, 53.34; H, 5.96; N, 17.31.

EXAMPLE II

Preparation of 1-(1,4-Dithiane-2-iminooxy)-7-(2,4-dimethylphenylimino)-2,4,6-triaza-2,4,6-trimethyl-3-thia-1,5-dioxoheptane (Step B, Method I)

To a stirred mixture of 1.79 g (0.012 m) of 2-oximino-1,4-dithiane and 3.92 g (0.012 m) of 1-fluoro-7-(2,4-dimethylphenylimino)-2,4,6-triaza-2,4,6-trimethyl-3-thia-1,5-dioxoheptane in 50 ml of toluene was added 1.21 g (0.012 m) of triethylamine. After heating at 50° C. for 16 hours, the reaction mixture was cooled, washed successively with water, dilute sodium hydroxide and water. The organic layer was dried and concentrated to a residual oil. This material was purified by dry-column chromatography using silica gel to afford 2.5 g of colorless viscous oil.

Calc'd for $C_{18}H_{25}N_5O_3S_3$: C, 47.45; H, 5.53; N, 15.37; Found: C, 57.62; H, 5.49; N, 15.34.

Additional compounds of the present invention (Examples VIII–XI below) were prepared in accordance with the procedure of Examples I and II above, using identical amounts of reactants and reaction conditions. Results are as follows:

Example VIII, 1-(3-Methyl-4-methylthiophenoxy)-7-(2,4-dimethylphenylimino)-2,4,6-triaza-2,4,6-trimethyl-3-thia-1,5-dioxoheptane:
Cal'd: C, 57.37; H, 6.13, N, 12.16. Found: C, 57.53; H, 6.00; N, 12.05.

Example IX, 1-(3-Isopropylphenoxy)-7-(2,4-dimethylphenylimino)-2,4,6-triaza-2,4,6-trimethyl-3-thia-1,5-dioxoheptane:
Cal'd: C, 62.42; H, 6.83; N, 12.66. Found: C, 62.31; H, 6.73; N, 12.63.

Example X, 1-(2-Isopropoxylphenoxy)-7-(2,4-dimethylphenylimino)-2,4,6-triaza-2,4,6-trimethyl-3-thia-1,5-dioxoheptane:
Cal'd: C, 60.24; H, 6.59; N, 12.22. Found: C, 59.89; H, 6.57; N, 12.20.

Example XI, 1-[4-(2,2-Dimethylbenzodioxalanoxy)]-7-(2,4-dimethylphenylimino)-2,4,6-triaza-2,4,6-trimethyl-3-thia-1,5-dioxoheptane:
Cal'd: C, 58.46; H, 5.97; N, 11.85. Found: C, 58.26; H, 5.91; N, 11.97.

EXAMPLE III

Preparation of 1-(2,4-Dimethylphenylimino)-2,4,6,9-tetraaza-2,4,6,10-tetramethyl-8-oxa-5,11-dithia-3,7-dioxo-dodeca-9-ene (Method II)

To a solution of 5.0 g (0.0186 m) of 1-methylthioacetaldehyde-O-[N-methyl-N-(N'-methyl-N'-fluorocarbonylaminosulfenyl)carbamoyl]oxime and 3.37 g (0.0208 m) of N-(2,4-dimethylphenyl)-N'-methylformamidine in 150 ml of toluene was added 2.10 g (0.0208 m) of triethylamine. After stirring at room temperature for 60 hours the reaction mixture was washed five times with water. The organic layer was dried over anhydrous magnesium sulfate and concentrated to afford 8.39 g of a clear viscous oil which crystallized on addition of isopropyl ether, m.p. 90°–92° C.

Calc'd for $C_{17}H_{25}N_5O_3S_2$: C, 49.61; H, 6.12, N, 17.02; Found: C, 49.50; H, 5.94; N, 16.86.

EXAMPLE IV

Preparation of 1-(4-Chloro-2-methylphenylimino)-2,4,6,9-tetraaza-2,4,6,10-tetramethyl-8-oxa-5,11-dithia-3,7-dioxo-dodeca-9-ene (Method II)

To a solution of 4.75 g (0.02 m) of 1-methylthioacetaldehyde-O-[N-methyl-N-(N'-methyl-N'-fluorocarbonylaminosulfenyl)carbamoyl]oxime and 3.65 g (0.02 m) of N-[4-Chloro-2-methylphenyl]-N'-methylformamidine in 100 ml of toluene was added 2.02 g (0.02 m) of triethylamine. After stirring for 66 hours the reaction mixture was washed successively with water, 5 percent sodium hydroxide solution and water. The organic layer was dried and concentrated to a residual oil. The product crystallized from a solution of isopropyl ether/ethyl acetate to afford 3.2 g of a white solid m.p. 110°–112° C.

Calc'd for $C_{16}H_{22}ClN_5O_3S_2$: C, 44.49; H, 5.13, N, 16.21; Found: C, 44.23; H, 4.96; N, 16.04.

EXAMPLE V

Preparation of 1-(1-Naphthyloxy)-7-(2,4-dimethylphenylimino)-2,4,6-triaza-2,4,6-trimethyl-3-thia-1,5-dioxoheptane (Method II)

To a solution of 2.0 g (0.0123 m) of N-(2,4-dimethylphenyl)-N'-methyl formamidine and 3.79 g (0.0123 m) of 1-[N-methyl-N-(N'-methyl-N'-fluorocarbonylaminosulfenyl)carbamoyloxy]naphthalene in 75 ml of toluene was added 1.2 g (0.0123 m) of triethylamine. After stirring at room temperature for 18 hours, the reaction mixture was diluted with 100 ml of toluene and was washed with water. The organic layer was dried over anhydrous magnesium sulfate and concentrated under reduced pressure to afford 4.7 g of an amber colored oil. The analytical sample was purified by dry column chromatography using silica gel.

Calc'd for $C_{24}H_{26}N_4O_3S$: C, 63.97; H, 5.82; N, 12.44; Found: C, 63.91; H, 5.75; N, 11.22.

EXAMPLE VI

Preparation of
1-[7-(2,3-Dihydro-2,2-dimethylbenzofuranyloxy)]-7-(2,4-dimethylphenylimino)-2,4,6-triaza-2,4,6-trimethyl-3-thia-1,5-dioxoheptane (Method II)

To a solution of 2.47 g (0.0152 m) of N-(2,4-dimethylphenyl)-N'-methylformamidine and 5.0 g (0.0152 m) of 2,3-dihydro-2,2-dimethyl-7-[N-methyl-N-(N'-methyl-N'-fluorocarbonylaminosulfenyl)carbamoyloxy]benzofuran in 150 ml of toluene was added 1.54 g (0.0152 m) of triethylamine. After stirring for 60 hours at room temperature the solution was washed four times with water and the organic layer was dried over anhydrous magnesium sulfate and concentrated under reduced pressure to afford 7.4 g of a brown viscous oil. The crude product was purified by chromatographic techniques using silica gel.

Calc'd for $C_{24}H_{30}N_4O_4S$: C, 61.25; H, 6.43; N, 11.91; Found: C, 61.48; H, 6.69; N, 10.84.

EXAMPLE VII

Preparation of
1-[7-(2,3-Dihydro-2,3-dimethylbenzofuranyloxy)]-7-(4-chloro-2-methylphenylimino)-2,4,6-triaza-2,4,6-trimethyl-3-thia-1,5-dioxoheptane (Method II)

To a solution of 2.74 g (0.015 m) of N-(4-chloro-2-methylphenyl)-N'-methylformamidine and 4.92 g (0.015 m) of 2,3-dihydro-2,2-dimethyl-7-[N-methyl-N-(N'-methyl-N'-fluorocarbonylaminosulfenyl)carbamoyloxy]benzofuran in 100 ml of toluene was added 1.52 g (0.015 m) of triethylamine dropwise with stirring. After stirring at room temperature for 72 hours, the reaction mixture was washed with water and the organic layer was dried over anhydrous magnesium sulfate and concentrated under reduced pressure to a clear viscous oil. Purification by dry column chromatography using silica gel afforded 6.07 g of the product as an oil.

Calc'd for $C_{23}H_{27}ClN_4O_4S$: C, 56.26; H, 5.54; N, 11.41. Found: C, 56.15; H, 5.54; N, 10.58.

The following compounds are illustrative of the compounds of this invention all of which can be conveniently prepared by any one of the processes of this invention simply by selecting appropriate starting materials:

1-(1-(5,6,7,8-Tetrahydro)naphthyloxy)-7-(2,4-dimethylphenylimino)-2,4,6-triaza-2,4,6-trimethyl-3-thia-1,5-dioxoheptane.

1-(1-(4-Dodecyl)phenoxy)-7-(2,4-dimethylphenylimino)-2,4,6-triaza-2,4,6-trimethyl-3-thia-1,5-dioxoheptane.

1-(1-(2-Ethylthiomethyl)phenoxy)-7-(4-chloro-2-methylphenylimino)-2,4,6-triaza-2,4,6-trimethyl-3-thia-1,5-dioxoheptane.

1-(1-(2-Propynyloxy)phenoxy)-7-(4-chloro-2-methylphenylimino)-2,4,6-triaza-2,4,6-trimethyl-3-thia-1,5-dioxoheptane 1-(1-(3-Methyl-4-N,N-dimethylformamidino)phenoxy)-7-(4-chloro-2-methylphenylimino)-2,4,6-triaza-2,4,6-trimethyl-3-thia-1,5-dioxoheptane.

1-(1-(3,5-Dimethyl-4-dimethylamino)phenoxy)-7-(2,4-dimethylphenylimino)-2,4,6-triaza-2,4,6-trimethyl-3-thia-1,5-dioxoheptane.

1-(1-(2,2(1,3-Dioxolanyl))phenoxy)-7-(4-chloro-2-methylphenylimino)-2,4,6-triaza-2,4,6-trimethyl-3-thia-1,5-dioxopheptane.

1-(1-(2-2(1,3-Dithiolanyl))phenoxy)-7-(2,4-dimethylphenylimino)-2,4,6-triaza-2,4,6-trimethyl-3-thia-1,5-dioxoheptane.

1-(1-(2-Chloro-4-bromo)phenoxy)-7-(2,4-dimethylphenylimino)-2,4,6-triaza-2,4,6-trimethyl-3-thia-1,5-dioxoheptane.

1-(1-(3-Isopropyl-4-methoxycarbonylamino)phenoxy)-7-(4-chloro-2-methylphenylimino)-2,4,6-triaza-2,4,6-trimethyl-3-thia-1,5-dioxoheptane.

1-(4-Chloro-2-methylphenylimino)-2,4,6,9-tetraaza-2,4,6,11,11-pentamethyl-8-oxa-5,12-dithia-3,7-dioxotrideca-9-ene.

1-(2,4-Dimethylphenylimino)-2,4,6,9-tetraaza-2,4,6-trimethyl-10-tert-butyl-8-oxa-5,12-dithia-3,7-dioxotrideca-9-ene 1-(4-Chloro-2-methylphenylimino)-2,3,6,9-tetraaza-2,4,6,10,11-pentamethyl-8-oxa-5-thia-12-sulfonyl-3,7-dioxotrideca-9-ene.

1-(2,4-Dimethylphenylimino)-2,4,6,9-tetraaza-2,4,6,10-tetramethyl-8-oxa-5,10-dithia-13-cyano-3,7-dioxotrideca-9-ene.

1-(2,4-Dimethylphenylimino)-2,4,6,9-tetraaza-2,4,6-trimethyl-10-methylthio-11-dimethylamino-8-oxa-5-thia-3,7,11-trioxoundeca-9-ene.

1-(2,4-Dimethylphenylimino)-2,4,6,9-tetraaza-2,4,6,11,11-pentamethyl-11-nitro-8-oxa-5-thia-3,7-dioxoundeca-9-ene.

1-(4-Chloro-2-methylphenylimino)-2,4,6,9-tetraaza-2,4,6-trimethyl-10-cyano-10-(2-chlorophenyl)-8-oxa-5-thia-3,7-dioxodeca-9-ene.

1-(4-Chloro-2-methylphenylimino)-2,4,6,9-tetraaza-2,4,6,11,11-pentamethyl-13-cyano-8-oxa-5-thia-3,7-dioxotrideca-9-ene.

1-(2,4-Dimethylphenylimino)-7-(1,3-dithiolane-2-iminooxy)-2,4,6-triaza-2,4,6-trimethyl-5-thia-3,7-dioxoheptane.

1-(4-Chloro-2-methylphenylimino)-7-(4,4-dimethyl-1,3-dithiolane-5-iminooxy)-2,4,6-triaza-2,4,6-trimethyl-5-thia-3,7-dioxoheptane.

1-(4-Chloro-2-methylphenylimino)-7-(3,5,5-trimethyl-4-thiazolidinone-2-iminooxy)-2,4,6-triaza-2,4,6-trimethyl-5-thia-3,7-dioxoheptane.

1-(2,4-Dimethylphenylimino)-7-(5-methyl-1,3-oxathiolane-4-iminooxy)-2,4,6-triaza-2,4,6-trimethyl-5-thia-3,7-dioxoheptane.

1-(4-Chloro-2-methylphenylimino)-7-(3,3,-dimethyl-1,4-dioxane-2-iminooxy)-2,4,6-triaza-2,4,6-trimethyl-5-thia-3,7-dioxoheptane.

1-(2,4-Dimethylphenylimino)-7-(4,5,5-trimethyl-3-thiazolidinone-2-iminooxy)-2,4,6-triaza-2,4,6-trimethyl-5-thia-3,7-dioxoheptane.

1-(2,4-Dimethylphenylimino)-7-(4,4-dimethyl-2-methylimino-1,3-dithiolane-5-iminooxy)-2,4,6-triaza-2,4,6-trimethyl-5-thia-3,7-dioxoheptane.

1-(4-Chloro-2-methylphenylimino)-7-(4-methyl-tetrahydro-1,4-thiazine-3-one-2-iminooxy)-2,4,6-triaza-2,4,6-trimethyl-5-thia-3,7-dioxoheptane.

1-(4-Chloro-2-methylphenylimino)-7-(3,3-dimethyl-1,4-oxathiane-2-iminooxy)-2,4,6-triaza-2,4,6-trimethyl-5-thia-3,7-dioxoheptane.

1-(2,4-Dimethylphenylimino)-7-(2,2-dimethylthiophane-3-iminooxy)-2,4,6-triaza-2,4,6-trimethyl-5-thia-3,7-dioxoheptane.

1-(4-Chloro-2-methylphenylimino)-2,4,7,10-tetraaza-2,4,7,11-tetramethyl-9-oxa-5,6,12-trithia-3,8-dioxotrideca-10-ene.

1-[7-(2,3-Dihydro-2,2-dimethylbenzofuranyloxy)]-8-(2,4-dimethylphenylimino)-2,5,7-triaza-2,5,7-trimethyl-3,4-dithia-1,6-dioxooctane.

1-[1-(3,5-Dimethyl-4-methylthiophenoxy)]-7-(4-chloro-2-methylphenylimino)-2,4,6-triaza-2,4,6-trimethyl-3-thia-1,5-dioxoheptane.

1-[1-(2-Isopropoxyphenoxy)]-7-(4-chloro-2-methylphenylimino)-2,4,6-triaza-2,4,6-trimethyl-3-thia-1,5-dioxoheptane.

1-[1-(2-Ethylthiomethylphenoxy)]-7-(2,4-dimethylphenylimino)-2,4,6-triaza-2,4,6-trimethyl-3-thia-1,5-dioxoheptane.

1-[1-(2-Ethylsulfinylmethylphenoxy)]-7-(2,4-dimethylphenylimino)-2,4,6-triaza-2,4,6-trimethyl-3-thia-1,5-dioxoheptane.

1-[1-(2-Ethylsulfonylmethylphenoxy)]-7-(4-chloro-2-methylphenylimino)-2,4,6-triaza-2,4,6-trimethyl-3-thia-1,5-dioxoheptane.

1-[1-(3,5-Dimethyl-4-methoxycarbonylaminophenoxy)]-7-(4-chloro-2-methylphenylimino)-2,4,6-triaza-2,4,6-trimethyl-3-thia-1,5-dioxoheptane.

1-[1-(4-Cyano-3-methylphenoxy)]-7-(4-chloro-2-methylphenylimino)-2,4,6-triaza-2,4,6-trimethyl-3-thia-1,5-dioxoheptane.

1-[4-(Benzothiophenoxy)]-7-(4-chloro-2-methylphenylimino)-2,4,6-triaza-2,4,6-trimethyl-3-thia-1,5-dioxoheptane.

1-[7-(2,3-Dihydro-2,2-dimethylbenzofuranyloxy)]-8-(2,4,6-trimethylphenylimino)-2,5,7-triaza-2,5,7-trimethyl-3,4-dithia-1,6-dioxooctane.

1-(4-Trifluoromethoxy-2-methylphenylimino)-2,4,6,9-tetraaza-2,4,6,10-tetramethyl-8-oxa-5,11-dithia-3,7-dioxo-dodeca-9-ene.

Selected species of the new compounds were evaluated to determine their pesticidal activity against mites, mite eggs, an aphid, a caterpillar, a beetle, a fly and a nematode.

Suspensions of the test compounds were prepared by dissolving one gram of compound in 50 ml of acetone in which had been dissolved 0.1 g (10 percent of the weight of the compound) of an alkylphenoxy polyethoxyethanol surfactant, as an emulsifying or dispersing agent. The resulting solution was mixed into 150 ml of water to give roughly 200 ml of a suspension containing the compound in finely divided form. The thus-prepared stock suspension contained 0.5 percent by weight of compound. The concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtrium plants at 68°–70° F. and 50±5 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids were placed on a revolving turntable and sprayed with 100–110 milliliters of test compound formulation by use of a DeVilbiss spray gun set at 40 psig air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 68°–70° F. and 50±5 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Spodoptera eridania*, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for three days. Although the larvae could easily consume the leaf within 24 to 48 hours, no more food was added. Larvae which were unable to move the length of the body, even upon stimulation, were considered dead.

Southern Armyworm Ovicide Test

The test organism was the egg of the Southern armyworm (*Spodoptera eridania* (Cram.)) as obtained from adults reared on Tendergreen bean plants at a temperature of 80°±5° F. and a relative humidity of 50±5 percent. The eggs were laid on freezer paper (Marlon 717, Copco paper). The paper was then cut into small sections containing one or two egg masses.

The test compounds were formulated by diluting the stock suspension with water to give a suspension containing 500 parts of test compound per million parts of final formulation. The egg masses were dipped until they were thoroughly wet (5–10 seconds). They were then placed on a paper towel face up and were allowed to dry for 15–30 minutes. The dry eggs were placed in a 15×60 mm petri dish containing a cotton dental wick saturated with a 5 percent sodium chloride solution to maintain a high level of humidity. The closed dishes were labeled and held at a temperature of 80°±5° F. for four days. Larvae that emerged from the eggs, even if dead at the time of observation, were recorded as hatched.

Mite Foliage Spray Test

Adults and nymphal stage of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 mites, a sufficient number for testing, were transferred from the excised leaves to the fresh plants in a period of twenty-four hours. Following the twenty-four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which last 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

Mite Ovicide Test

The test organism was the egg of the two-spotted mite (*Tetranychus urticae* Koch) as obtained from adults reared on Tendergreen bean plants under controlled conditions of 80°±5° F. and 50±5 percent relative humidity. Heavily infested leaves from a stock culture were placed on the primary leaves of 2 bean plants 6 to 8 inches in height, growing in a 2-¼ inch clay pot. Females were allowed to oviposit for a period of 48 hours and then the leaves of the infested plants were dipped in a solution containing 800 parts of tetraethyl pyrophosphate per million parts of water in order to destroy the reproductive forms and thus prevent further egg-laying. This solution of tetraethyl pyrophosphate does not affect the viability of the eggs. The plants were allowed to dry thoroughly.

The potted plants (one pot per compound) were placed on a revolving turntable and sprayed with 100–110 milliliters of test compound formulation by use of a DeVilbiss spray gun set at 40 psig air pressure. This application, which lasted 30 seconds, was sufficient to wet the plants to run-off. As a control, 100–110 milliliters of a water solution containing acetone and emulsifier in the same concentrations as the test compound formulation, but containing no test compound, were also sprayed on plants infested with eggs. The sprayed plants were held at 80°±5° F. and 50±5 percent relative humidity for 6 days, after which a microscopic examination was made of unhatched (dead) and hatched (living) eggs. Percent mortality was recorded for various concentration levels.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty-five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty-four hours, at a temperature of 80°±5° F. and a relative humidity of 50±5 percent. Flies which showed no sign of movement on prodding were considered dead.

Nematocide Test

The test organism used was the infective migratory larvae of the root-knot nematode, *Meloidogyne incognita* var. *acrita*, reared in the greenhouse on roots of cucumber plants. Infected plants were removed from the culture, and the roots chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone, addition of an emulsifier, and dilution with water. Primary screening tests were conducted at 3.33 mg. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots, and the amount of galling visually rated.

The results of these tests are set forth in Table I below. In these tests the pesticidal activity of the compounds at the indicated dosage rate against aphid, mite, Southern Armyworm, Bean Beetle, and housefly was rated as follows:

A = excellent control
B = partial control
C = no control at 500 ppm.

In the test for activity against nematodes activity was rated as follows:

1 = severe galling, equal to untreated plants
2 = moderate galling
3 = light galling
4 = very light galling
5 = no galling, perfect control
Dashes indicate no test conducted.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Non-ionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by

TABLE II

| Example Number | Bean Aphid | Two-Spotted Mite (Adult) | Two-Spotted Mite (Egg) | Southern Armyworm (Larvae) | Southern Armyworm (Egg) | Mexican Bean Beetle | Housefly | Nematodes |
|---|---|---|---|---|---|---|---|---|
| II | A | A | A | A | *— | A | A | 3 |
| III | A | A | B | A | — | A | A | 5 |
| IV | A | A | B | A | A | A | A | 1 |
| V | B | C | C | A | — | A | B | 1 |
| VI | A | A | C | A | — | A | A | 4 |
| VII | A | C | C | A | A | A | A | 4 |
| VIII | C | C | C | A | — | A | A | 1 |
| IX | B | B | — | A | A | A | A | 1 |
| X | A | C | C | B | — | A | A | 1 |
| XI | C | C | C | A | A | A | A | 1 |
| 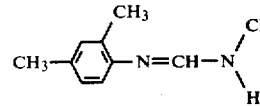 (comparison) | C | A | A | A | — | C | C | 1 |

*Dashes indicate no test conducted.

The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

insects, nematodes, mites and mite and insect ova upon plants or other material to which the pesticides are applied. Generally, when used in sufficient amount to kill or repel the insects, they do not burn or injure the plant. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds.

What is claimed is:

1. Compounds of the formula:

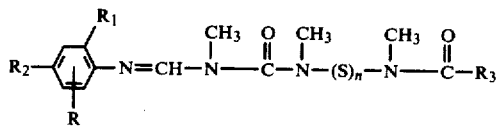

wherein:
n is 1 or 2;
R is hydrogen, halogen or alkyl;
$R_1$ and $R_2$ are individually halogen, alkyl, trihaloalky or di- or trihaloalkoxy; provided that the total number of carbon atoms in any one of R; $R_1$ or $R_2$ may not exceed four;
$R_3$ is:
  A. fluorine;
  B. phenoxy, which may be unsubstituted or substituted with one or more alkyl, chloro, fluoro, bromo, alkoxy, alkylthio, alkythioalkyl, alkylsulfinyl, alkylsulfinylalkyl, alkylsulfonyl, alkylsulfonylalkyl, alkynyloxy, dialkylamino, alkoxycarbonylamino, N,N-dialkyl formamidino, cyano, dioxolanyl, or dithiolanyl substituents in any combination; provided that the total number of aliphatic carbon atoms in $R_3$ does not exceed twelve;
  C. 1-naphthoxy, tetrahydronaphthoxy, dihydrobenzofuranoxy, benzodioxalanoxy, or benzothienoxy, any of which may be unsubstituted or substituted with one or more alkyl substituents; provided that the total number of aliphatic carbon atoms in $R_3$ does not exceed twelve;
  D.

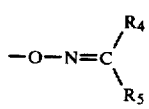

wherein:
$R_4$ is chloro, alkyl, alkylthio, cyanoalkylthio, cyano or hydrogen;
$R_5$ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstituted or substituted with one or more alkyl, chloro or fluoro substituents in any combination; provided that $R_4$ and $R_5$ are not both hydrogen; and provided further that the total number of aliphatic carbon atoms in $R_4$ and $R_5$ together does not exceed twelve; or
E.

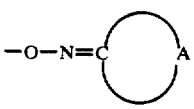

wherein:

A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximino-thiazolidin-3-one, 2-oximino-1,3-thiazolidin-4-one or 2-oximinotetrahydro-1,4-thiazin-5-one ring structure, all of which may be unsubstituted or substituted with one or more alkyl substituents.

2. A compound in accordance with claim 1 wherein n is 1.

3. A compound in accordance with claim 1 wherein n is 2.

4. A compound in accordance with claim 1 wherein $R_1$ and $R_2$ are both alkyl.

5. A compound in accordance with claim 1 wherein $R_1$ is alkyl and $R_2$ is a halogen.

6. A compound in accordance with claim 1 wherein $R_1$ is methyl and $R_2$ is chloro.

7. A compound in accordance with claim 1 wherein $R_1$ and $R_2$ are both methyl.

8. A compound in accordance with claim 1 wherein $R_3$ is fluorine.

9. A compound in accordance with claim 1 wherein $R_3$ is dihydrobenzofuranoxy substituted with alkyl groups.

10. A compound in accordance with claim 1 wherein $R_3$ is:

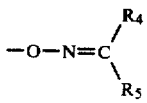

wherein $R_4$ is alkyl and $R_5$ is alkylthio.

11. A compound of the formula:

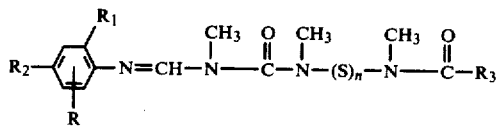

wherein:
n is 1 or 2;
R is hydrogen, halogen or alkyl;
$R_1$ and $R_2$ are individually halogen, alkyl, trihaloalky or di- or trihaloalkoxy; provided that the total number of carbon atoms in any one of R, $R_1$ or $R_2$ may not exceed four;
$R_3$ is:
  A. phenoxy which may be unsubstituted or substituted with one or more alkyl, chloro, fluoro, bromo, alkoxy, alkylthio, alkythioalkyl, alkylsulfinyl, alkylsulfinylalkyl, alkylsulfonyl, alkylsulfonylalkyl alkynyloxy, dialkylamino, alkoxycarbonylamino, N,N-dialkyl formamidino, cyano, dioxolanyl, or dithiolanyl substituents in any combination; provided that the total number of aliphatic carbon atoms in $R_3$ does not exceed twelve;
  B. 1-naphthoxy, tetrahydronaphthoxy, dihydrobenzofuranoxy, benzodioxalanoxy, or benzothienoxy, any of which may be unsubstituted or substituted with one or more alkyl moieties; provided that the total number of aliphatic carbon atoms in $R_3$ does not exceed twelve;

C.

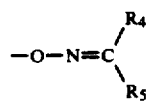

wherein:
$R_4$ is chloro, alkyl, alkylthio, cyanoalkylthio, cyano or hydrogen;
$R_5$ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstituted or substituted with one or more alkyl, chloro or fluoro substituents in any combination; provided that $R_4$ and $R_5$ may not both be hydrogen; provided that $R_4$ and $R_5$ may not both be hydrogen; and provided further that the total number of aliphatic carbon atoms in $R_4$ and $R_5$ together does not exceed twelve;

D.

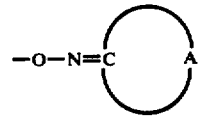

wherein:
A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximinothiazolidin-3-one, 2-oximino-1,3-thiazolidin-4-one or 2-oximinotetrahydro-1,4-thiazin-5-one ring structure, all of which may be unsubstituted or substituted with one or more alkyl substituents.

12. Compounds of the formula:

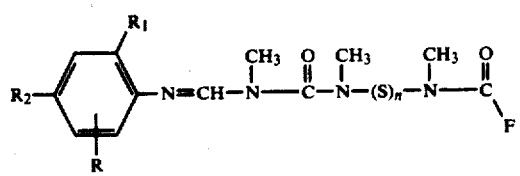

wherein:
n is 1 or 2;
R is hydrogen, halogen or alkyl;
$R_1$ and $R_2$ are individually alkyl, trihaloalkyl or di- or trihaloalkoxy; provided that the total number of carbon atoms in any one of R, $R_1$ or $R_2$ may not exceed four.

13. A compound in accordance with claim 12 wherein n is 1.
14. A compound in accordance with claim 12 wherein $R_1$ and $R_2$ are both alkyl.
15. A compound in accordance with claim 12 wherein $R_1$ is alkyl and $R_2$ is a halogen.
16. A compound in accordance with claim 12 wherein $R_1$ is methyl and $R_2$ is chloro.
17. A compound in accordance with claim 12 wherein $R_1$ and $R_2$ are both methyl.
18. Compounds of the formula:

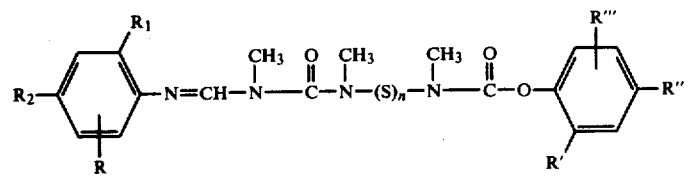

wherein:
n is 1 or 2;
R is hydrogen, halogen or alkyl;
$R_1$ and $R_2$ are individually halogen, alkyl, trihaloalkyl or di- or trihaloalkoxy; provided that the total number of carbon atoms in any one of R, $R_1$ or $R_2$ may not exceed four;
R', R" and R'" are individually hydrogen, alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxycarbonylamino, N,N-dialkyl formamidino, cyano, dioxolanyl, or dithiolanyl substituents; provided that the total number of aliphatic carbon atoms in any one of R', R" or R'" does not exceed twelve.

19. Compounds of the formula:

R₂—⟨⟩—N=CH—N(CH₃)—C(O)—N(CH₃)—(S)ₙ—N(CH₃)—C(O)—R₃ wherein:
n is 1 or 2;
R is hydrogen, halogen or alkyl;
$R_1$ and $R_2$ are individually halogen, alkyl, trihaloalkyl or di- or trihaloalkoxy; provided that the total number of carbon atoms in any one of R, $R_1$ or $R_2$ may not exceed four;
$R_3$ is 1-naphthoxy, tetrahydronaphthoxy, dihydrobenzofuranoxy, benzodioxalanoxy, or benzothienoxy, any of which may be unsubstituted or substituted with one or more alkyl substituents; provided that the total number of aliphatic carbon atoms in $R_3$ does not exceed twelve.

20. A compound in accordance with claim 19 wherein $R_3$ is dihydrobenzofuranoxy, unsubstituted or substituted with one or more alkyl substituents.

21. Compounds of the formula:

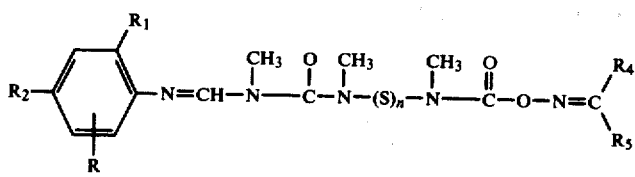

wherein:

n is 1 or 2;

R is hydrogen, halogen or alkyl;

$R_1$ and $R_2$ are individually halogen, alkyl, trihaloalky or di- or trihaloalkoxy; provided that the total number of carbon atoms in any one of R, $R_1$ or $R_2$ may not exceed four;

$R_4$ is chloro, alkyl, alkylthio, cyanoalkylthio, cyano or hydrogen;

$R_5$ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstituted or substituted with one or more alkyl, chloro or fluoro substituents in any combination; provided that $R_4$ and $R_5$ are not both hydrogen; and provided further that the total number of aliphatic carbon atoms in $R_4$ and $R_5$ together does not exceed twelve.

22. A compound in accordance with claim 20 wherein $R_4$ is alkyl and $R_5$ is alkylthio.

23. Compounds of the formula:

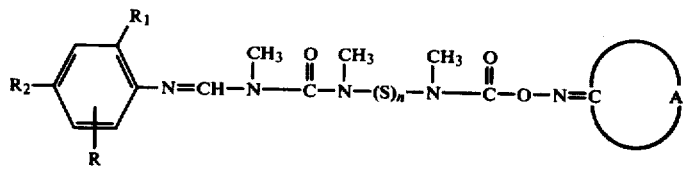

wherein:

n is 1 or 2;

R is hydrogen, halogen or alkyl;

$R_1$ and $R_2$ are individually halogen, alkyl, trihaloalky or di- or trihaloalkoxy; provided that the total number of carbon atoms in any one of R, $R_1$ or $R_2$ may not exceed four;

A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximino-thiazolidin-3-one, 2-oximino-1,3-thiazolidin-4-one or 2-oximino-tetrahydro-1,4-thiazin-5-one ring structure, all of which may be unsubstituted or substituted with one or more alkyl substituents.

24. 1-Fluoro-7-(2,4-dimethylphenylimino)-2,4,6-triaza-2,4,6-trimethyl-3-thia-1,5-dioxoheptane.

25. 1-Fluoro-7-(4-chloro-2-methylphenylimino)-2,4,6-triaza-2,4,6-trimethyl-3-thia-1,5-dioxoheptane.

26. 1-[7-(2,3-Dihydro-2,2-dimethylbenzofuranyloxy)]-7-(4-chloro-2-methylphenylimino)-2,4,6-triaza-2,4,6-trimethyl-3-thia-1,5-dioxoheptane.

27. 1-(4-Chloro-2-methylphenylimino)-2,4,6,9-tetraaza-2,4,6,10-tetramethyl-8-oxa-5,11-dithia-3,7-dioxododeca-9-ene.

28. A method for preparing a compound of the formula:

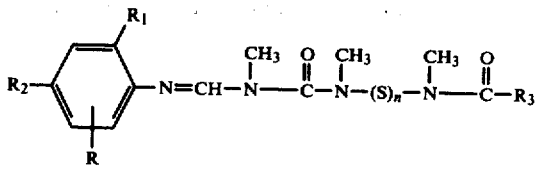

which comprises reacting a compound of the formula:

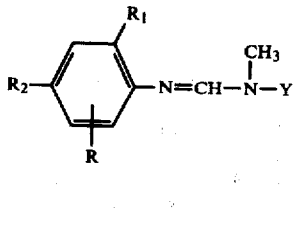

with a compound of the formula:

$R_3$-Z in the presence of an inorganic or organic acid acceptor wherein:

n is 1 or 2;

R is hydrogen, halogen or alkyl;

$R_1$ and $R_2$ are individually halogen, alkyl, trihaloalkyl or di- or trihaloalkoxy; provided that the total number of carbon atoms in any one of R, $R_1$ or $R_2$ may not exceed four;

$R_3$ is:

A. fluorine,

B. phenoxy which may be unsubstituted or substituted with one or more alkyl, chloro, fluoro, bromo, alkoxy, alkylthio, alkythioalkyl, alkylsulfinyl, alkylsulfinylalkyl, alkylsulfonyl, alkylsulfonylalkyl, alkynyloxy, dialkylamino, alkoxycarbonylamino, N-N-dialkyl formamidino, cyano, dioxolanyl, or dithiolanyl substituents in any combination; provided that the total number of aliphatic carbon atoms in $R_3$ does not exceed twelve, C. 1-naphthoxy, tetrahydronaphthoxy, dihydrobenzofuranoxy, benzodioxalanoxy, or benzothienoxy, any of which may be unsubstituted or substituted with one or more alkyl substituents; provided that the total number of aliphatic carbon atoms in R₃ does not exceed twelve;

D.

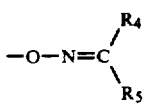

wherein:

R₄ is chloro, alkyl, alkylthio, cyanoalkylthio, cyano or hydrogen;

R₅ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstituted or substituted with one or more alkyl, chloro or fluoro substituents in any combination; provided that R₄ and R₅ may not both be hydrogen; and provided further that the total number of aliphatic carbon atoms in R₄ and R₅ together does not exceed twelve; or

E.

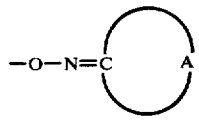

wherein:

A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximino-thiazolidin-3-one, 2-oximino-1,3-thiazolidin-4-one or 2-oximinotetrahydro-1,4-thiazin-5-one ring structure, all of which may be unsubstituted or substituted with one or more alkyl substituents;

Y and Z are individually hydrogen or

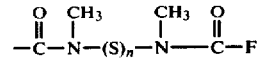

provided that they may not both be hydrogen or both

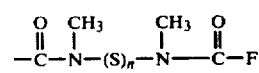

and provided further that when R₃ is fluorine Z may not be hydrogen.

29. A method for preparing a compound of the formula:

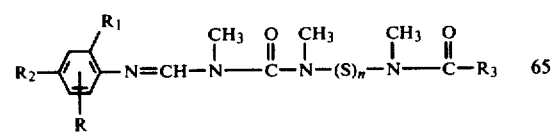

which comprises reacting a compound of the formula:

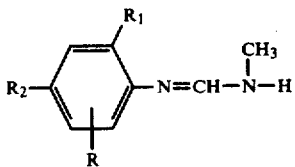

with a compound of the formula:

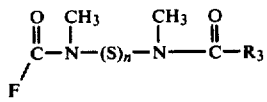

in the presence of an inorganic or organic acid acceptor wherein:

n is 1 or 2;

R is hydrogen, halogen or alkyl;

R₁ and R₂ are individually halogen, alkyl, trihaloalkyl or di- or trihaloalkoxy; provided that the total number of carbon atoms in any one of R, R₁ or R₂ may not exceed four;

R₃ is:

A. fluorine,

B. phenoxy which may be unsubstituted or substituted with one or more alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxycarbonylamino, N-N-dialkyl formamidino, cyano, dioxolanyl, or dithiolanyl substituents in any combination; provided that the total number of aliphatic carbon atoms in R₃ does not exceed twelve, C. 1-naphthoxy, tetrahydronaphthoxy, dihydrobenzofuranoxy, benzodioxalanoxy, or benzothienoxy, any of which may be unsubstituted or substituted with one or more alkyl substituents; provided that the total number of aliphatic carbon atoms in R₃ does not exceed twelve;

D.

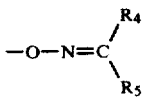

wherein:

R₄ is chloro, alkyl, alkylthio, cyanoalkylthio, cyano or hydrogen;

R₅ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstituted or substituted with one or more alkyl, chloro or fluoro substituents in any combination; provided that R₄ and R₅ may not both be hydrogen; and provided further that the total number of aliphatic carbon atoms in R₄ and R₅ does not exceed twelve:

E.

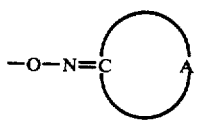

wherein:

A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximino-thiazolidin-3-one, 2-oximino-1,3-thiazolidin-4-one or 2-oximinotetrahydro-1,4-thiazin-5-one ring structure, all of which may be unsubstituted or substituted with one or more alkyl substituents.

30. A method for preparing a compound of the formula:

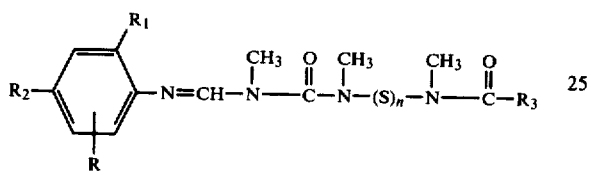

which comprises reacting a compound of the formula:

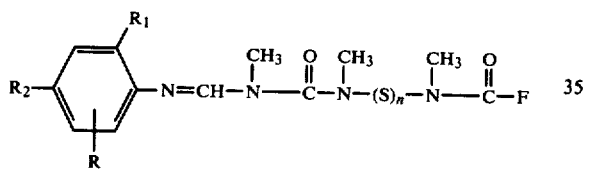

with a compound of the formula:

$R_3H$ in the presence of an inorganic or organic acid acceptor wherein:

n is 1 or 2;

R is hydrogen, halogen or alkyl;

$R_1$ and $R_2$ are individually halogen, alkyl, trihaloalkyl or di- or trihaloalkoxy; provided that the total number of carbon atoms in any one of R, $R_1$ or $R_2$ may not exceed four;

$R_3$ is:

A. phenoxy which may be unsubstituted or substituted with one or more alkyl, chloro, fluoro, bromo, alkoxy, alkylthio, alkythioalkyl, alkylsulfinyl, alkylsulfinylalkyl, alkylsulfonyl, alkylsulfonylalkyl, alkynyloxy, dialkylamino, alkoxycarbonylamino, N-N-dialkyl formamidino, cyano, dioxolanyl, or dithiolanyl substituents in any combination; provided that the total number of aliphatic carbon atoms in $R_3$ does not exceed twelve, B. 1-naphthoxy, tetrahydronaphthoxy, dihydrobenzofuranoxy, benzodioxalanoxy, or benzothienoxy, any of which may be unsubstituted or substituted with one or more alkyl substituents; provided that the total number of aliphatic carbon atoms in $R_3$ does not exceed twelve;

C.

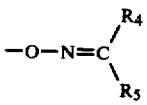

wherein:

$R_4$ is chloro, alkyl, alkylthio, cyanoalkylthio, cyano or hydrogen;

$R_5$ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstituted or substituted with one or more alkyl, chloro or fluoro substituents in any combination; provided that $R_4$ and $R_5$ may not both be hydrogen; and provided further that the total number of aliphatic carbon atoms in $R_4$ and $R_5$ together does not exceed twelve;

D.

 A wherein:

A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximino-thiazolidin-3-one, 2-oximino-1,3-thiazolidin-4-one or 2-oximinotetrahydro-1,4-thiazin-5-one ring structure, all of which may be unsubstituted or substituted with one or more alkyl substituents.

31. An insecticidal, miticidal and nematocidal composition comprising an acceptable carrier and as the active toxicant an insecticidally, miticidally or nematocidally effective amount of a compound of the formula:

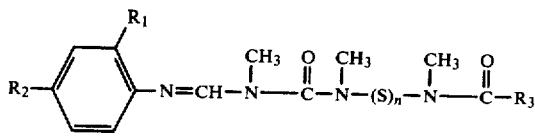

wherein:

n is 1 or 2;

R is hydrogen, halogen or alkyl;

$R_1$ and $R_2$ are individually halogen, alkyl, trihaloalky or di- or trihaloalkoxy; provided that the total number of carbon atoms in any one of R, $R_1$ or $R_2$ may not exceed four;

$R_3$ is:

A. fluorine,

B. phenoxy which may be unsubstituted or substituted with one or more alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxycarbonylamino, N,N-dialkyl formamidino, cyano, dioxolanyl, or dithiolanyl substituent in any combination; provided that the total number of aliphatic carbon atoms in R₃ does not exceed twelve;

C. 1-naphthoxy, tetrahydronaphthoxy, dihydrobenzofuranoxy, benzodioxalanoxy, or benzothienoxy, any of which may be unsubstituted or substituted with one or more alkyl moieties; provided that the total number of aliphatic carbon atoms in R₃ does not exceed twelve;

D.

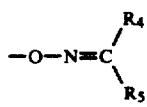

wherein:
R₄ is chloro, alkyl, alkylthio, cyanoalkylthio, cyano or hydrogen;
R₅ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstitued or substituted with one or more alkyl, chloro or fluoro substituents in any combination; provided that R₄ and R₅ may not both be hydrogen; provided that R₄ and R₅ may not both be hydrogen; and provided further that the total number of aliphatic carbon atoms in R₄ and R₅ together does not exceed twelve; or

E.

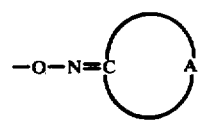

wherein:
A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximinothiazolidin-3-one, 2-oximino-1,3-thiazolidin-4-one or 2-oximino-tetrahydro-1,4-thiazin-5-one ring structure, all of which may be unsubstituted or substituted with one or more alkyl substituents.

32. A composition in accordance with claim 31 wherein n is 1.

33. A composition in accordance with claim 31 wherein n is 2.

34. A composition in accordance with claim 31 wherein R₁ and R₂ are both alkyl.

35. A composition in accordance with claim 31 where R₁ is alkyl and R₂ is a halogen.

36. A composition in accordance with claim 31 where R₁ is methyl and R₂ is chloro.

37. A composition in accordance with claim 31 wherein R₁ and R₂ are both methyl.

38. A composition in accordance with claim 31 wherein R₃ is fluorine.

39. A composition in accordance with claim 31 wherein R₃ is dihydrobenzofuranoxy substituted with alkyl groups.

40. A composition in accordance with claim 31 wherein R₃ is:

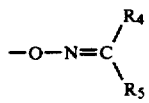

wherein R₄ is alkyl and R₅ is alkylthio.

41. An insecticidal, miticidal and nematocidal composition comprising an acceptable carrier and as the active toxicant an insecticidally, miticidally or nematocidally effective amount of a compound of the formula:

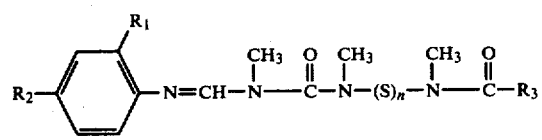

wherein:
n is 1 or 2;
R is hydrogen, halogen or alkyl;
R₁ and R₂ are individually halogen, alkyl, trihaloalky or di- or trihaloalkoxy; provided that the total number of carbon atoms in any one of R, R₁ or R₂ may not exceed four;
R₃ is:
A. phenoxy which may be unsubstituted or substituted with one or more alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxycarbonylamino, N,N-dialkyl formamidino, cyano, dioxolanyl, or dithiolanyl substituents in any combination; provided that the total number of aliphatic carbon atoms in R₃ does not exceed twelve;
B. 1-naphthoxy, tetrahydronaphthoxy, dihydrobenzofuranoxy, benzodioxalanoxy, or benzothienoxy, any of which may be unsubstituted or substituted with one or more alkyl moieties; provided that the total number of aliphatic carbon atoms in R₃ does not exceed twelve;

C.

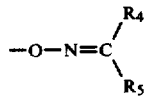

wherein:
R₄ is chloro, alkyl, alkylthio, cyanoalkylthio, cyano or hydrogen;
R₅ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstituted or substituted with one or more alkyl, chloro or fluoro substituents in any combination; provided that R₄ and R₅ may not both be hydrogen; provided that R₄ and R₅ may not both be hydrogen; and provided further that the total number of aliphatic carbon atoms in $R_4$ and $R_5$ together does not exceed twelve; or

D.

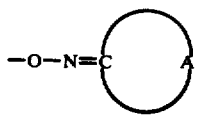

wherein:

A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximino-thiazolidin-3-one, 2-oximino-1,3-thiazolidin-4-one or 2-oximinotetrahydro-1,4-thiazin-5-one ring structure, all of which may be unsubstituted or substituted with one or more alkyl substituents.

42. An insecticidal, miticidal, and nematocidal composition comprising an acceptable carrier and as the active toxicant an insecticidally, miticidally or nematocidally effective amount of a compound of the formula:

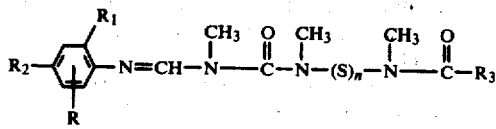

wherein:
n is 1 or 2;
R is hydrogen, halogen or alkyl;
$R_1$ and $R_2$ are individually halogen, alkyl, trihaloalky or di- or trihaloalkoxy; provided that the total number of carbon atoms in any one of R, $R_1$ or $R_2$ may not exceed four;
$R_3$ is 1-naphthoxy, tetrahydronaphthoxy, dihydrobenzofuranoxy, benzodioxalanoxy, or benzothienoxy, any of which may be unsubstituted or substituted with one or more alkyl moieties, provided that the total number of aliphatic carbon atoms in $R_3$ does not exceed twelve.

44. A composition in accordance with claim 43 wherein $R_3$ is dihydrobenzofuranoxy, unsubstituted or substituted with one or more alkyl substituents.

45. An insecticidal, miticidal and nematocidal composition comprising an acceptable carrier and as the active toxicant an insecticidally, miticidally or nematocidally effective amount of a compound of the formula:

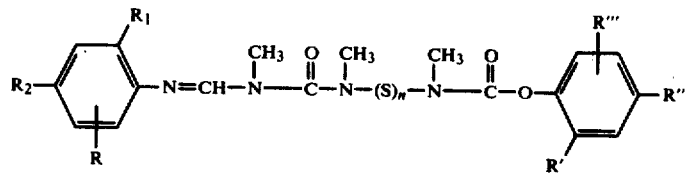

wherein:

n is 1 or 2;
R is hydrogen, halogen or alkyl;
$R_1$ and $R_2$ are individually halogen, alkyl, trihaloalkyl or di- or trihaloalkoxy; provided that the total number of carbon atoms in any one of R, $R_1$ or $R_2$ may not exceed four;
R', R" and R''' are individually hydrogen, alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxycarbonylamino, formamidino, cyano, dioxolanyl, or dithiolanyl substituent; provided that the total number of aliphatic carbon atoms in any one of R', R" and R''' does not exceed twelve.

43. An insecticidal, miticidal and nematocidal composition comprising an acceptable carrier and as the active toxicant an insecticidally, miticidally or nematocidally effective amount of a compound of the formula:

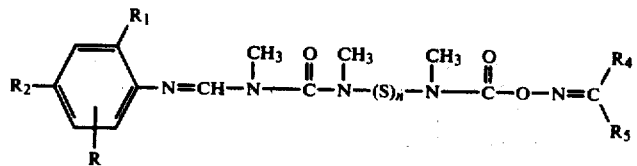

n is 1 or 2
R is hydrogen, halogen or alkyl; trihaloalky or di- or trihaloalkoxy; provided that the total number of carbon atoms in any one of R, $R_1$ or $R_2$ may not exceed four;
$R_4$ is chloro, alkyl, alkylthio, cyanoalkylthio, cyano or hydrogen;
$R_5$ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstituted or substituted with one or more alkyl, chloro or fluoro substitutes in any combination; provided that $R_4$ and $R_5$ are not both hydrogen.

46. A composition in accordance with claim 45 wherein $R_4$ is alkyl and $R_5$ is alkylthio.

47. An insecticidal, miticidal and nematocidal composition comprising an acceptable carrier and as the active toxicant an insecticidally, miticidally or nematocidally effective amount of a compound of the formula:

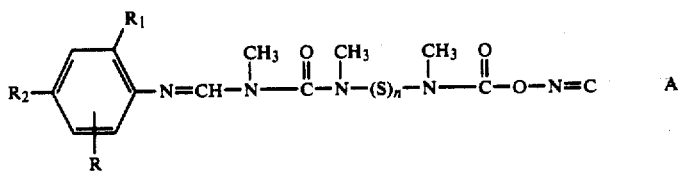

wherein:
n is 1 or 2;
R is hydrogen, halogen or alkyl;
$R_1$ and $R_2$ are individually halogen, alkyl, trihaloalky or di- or trihaloalkoxy; provided that the total number of carbon atoms in any one of R, $R_1$ or $R_2$ may not exceed four;
A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximinothiazolidin-3-one, 2-oximino-1,3-thiazolidin-4-one or 2-oximinotetrahydro-1,4-thiazin-5-one ring structure, all of which may be unsubstituted or substituted with one or more alkyl substituents.

48. An insecticidal, miticidal and nematocidal composition comprising an acceptable carrier and as the active toxicant an insecticidally, miticidally or nematocidally effective amount of 1-[7-(2,3-Dihydro-2,2-dimethylbenzofuranyloxy)]-7-(4-chloro-2-methylphenylimino)-2,4,6-triaza-2,4,6-trimethyl-3-thia-1,5-dioxoheptane.

49. An insecticidal, miticidal and nematocidal composition comprising an acceptable carrier and as the active toxicant an insecticidally, miticidally or nematocidally effective amount of 1-(4-Chloro-2-methylphenylimino)-2,4,6,9-tetraaza-2,4,6,10-tetramethyl-8-oxa-5,11-dithia-3,7-dioxododeca-9-ene.

50. A method of controlling insects, mites and nematodes which comprises subjecting them to an insecticidally, miticidally or nematocidally effective amount of a compound of the formula:

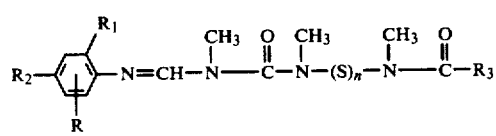

wherein:
n is 1 or 2;
R is hydrogen, halogen or alkyl;
$R_1$ and $R_2$ are individually halogen, alkyl, trihaloalkyl or di- or trihaloalkoxy; provided that the total number of carbon atoms in any one of R, $R_1$ or $R_2$ may not exceed four;
$R_3$ is:
A. fluorine,
B. phenoxy which may be unsubstituted or substituted with one or more alkyl, chloro, fluoro, bromo, alkoxy, alkylthio, alkythioalkyl, alkylsulfinyl, alkylsulfinylalkyl, alkylsulfonyl, alkylsulfonylalkyl, alkynyloxy, dialkylamino, alkoxycarbonylamino, N,N-dialkyl formamidino, cyano, dioxolanyl, or dithiolanyl substituent in any combination; provided that the total number of aliphatic carbon atoms in $R_3$ does not exceed twelve;

C. 1-naphthoxy, tetrahydronaphthoxy, dihydrobenzofuranoxy, benzodioxalanoxy, or benzothienoxy group, any of which may be unsubstituted or substituted with one or more alkyl substituents; provided that the total number of aliphatic carbon atoms in $R_3$ does not exceed twelve;

D.

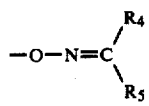

wherein:
$R_4$ is chloro, alkyl, alkylthio, cyanoalkylthio, cyano or hydrogen,
$R_5$ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstitued or substituted with one or more alkyl, chloro or fluoro substituents in any combination; provided that $R_4$ and $R_5$ may not both be hydrogen; and provided further that the total number of aliphatic carbon atoms in $R_4$ and $R_5$ together does not exceed twelve; or

E.

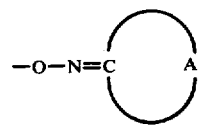

wherein:
A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximinothiazolidin-3-one, 2-oximino-1,3-thiazolidin-4-one or 2-oximinotetrahydro-1,4-thiazin-5-one ring structure, all of which may be unsubstituted or substituted with one or more alkyl substituents.

51. A method in accordance with claim 50 wherein n is 1.

52. A method in accordance with claim 50 wherein n is 2.

53. A method in accordance with claim 50 wherein $R_1$ and $R_2$ are both alkyl.

54. A method in accordance with claim 50 wherein $R_1$ is alkyl and $R_2$ is a halogen.

55. A method in accordance with claim 50 wherein $R_1$ is methyl and $R_2$ is chloro.

56. A method in accordance with claim 50 wherein $R_1$ and $R_2$ are both methyl.

57. A method in accordance with claim 50 wherein $R_3$ is fluorine.

58. A method in accordance with claim 50 wherein $R_3$ is dihydrobenzofuranoxy substituted with alkyl substituents.

59. A method in accordance with claim 50 wherein $R_3$ is:

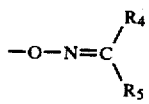

wherein $R_4$ is alkyl and $R_5$ is alkylthio.

60. A method of controlling insects, mites and nematodes which comprises subjecting them to an insecticidally, miticidally or nematocidally effective amount of a compound of the formula:

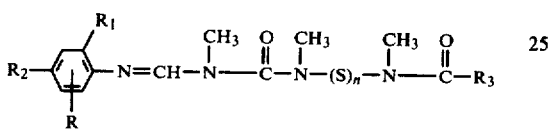

wherein:
n is 1 or 2;
R is hydrogen, halogen or alkyl;
$R_1$ and $R_2$ are individually halogen, alkyl, trihaloalkyl or di- or trihaloalkoxy; provided that the total number of carbon atoms in any one of R, $R_1$ or $R_2$ may not exceed four;
$R_3$ is:
A. phenoxy which may be unsubstituted or substituted with one or more alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, alkoxycarbonylamino, N,N-dialkyl formamidino, cyano, dioxolanyl, or dithiolanyl substituents in any combination; provided that the total number of aliphatic carbon atoms in $R_3$ does not exceed twelve;
B. 1-naphthoxy, tetrahydronaphthoxy, dihydrobenzofuranoxy, benzodioxalanoxy, or benzothienoxy, any of which may be unsubstituted or substituted with one or more alkyl moieties; provided that the total number of aliphatic carbon atoms in $R_3$ does not exceed twelve;
C.

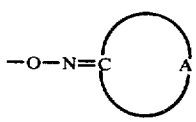

wherein:
$R_4$ is chloro, alkyl, alkylthio, cyanoalkylthio, cyano or hydrogen;
$R_5$ is alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen, said phenyl being unsubstituted or substituted with one or more alkyl, chloro or fluoro substituents in any combination; provided that $R_4$ and $R_5$ may not both be hydrogen; provided that $R_4$ and $R_5$ may not both be hydrogen; and provided further that the total number of aliphatic carbon atoms in $R_4$ and $R_5$ together does not exceed twelve; or
D.

$$-O-N=C\overset{\displaystyle\bigcirc}{\phantom{X}}A$$

wherein:
A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximino-thiazolidin-3-one, 2-oximino-1,3-thiazolidin-4-one or 2-oximinotetrahydro-1,4-thiazin-5-one ring structure, all of which may be unsubstituted or substituted with one or more alkyl substituents.

61. A method of controlling insects, mites and nematodes which comprises subjecting them to an insecticidally, miticidally or nematocidally effective amount of a compound of the formula:

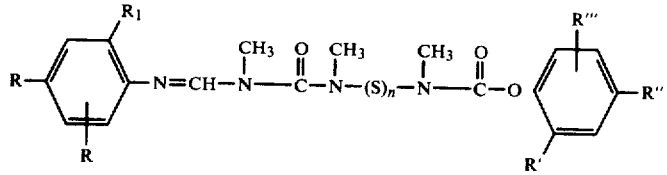

wherein:
n is 1 or 2;
R is hydrogen, halogen or alkyl;
$R_1$ and $R_2$ are individually halogen, alkyl, trihaloalkyl or di- or trihaloalkoxy; provided that the total number of carbon atoms in any one of R, $R_1$ or $R_2$ may not exceed four;
R', R" and R'" are individually hydrogen, alkyl, chloro, fluoro, bromo, alkoxy, alkylthio, alkylthioalkyl, alkylsulfinyl, alkylsulfinylalkyl, alkylsulfonyl, alkylsulfonylalkyl, alkynyloxy, dialkylamino, or dithiolanyl substituents; provided that the total number of aliphatic carbon atoms in any one of R', R" or R'" does not exceed twelve.

62. A method of controlling insects, mites and nematodes which comprises subjecting them to an insecticidally, miticidally or nematocidally effective amount of a compound of the formula:

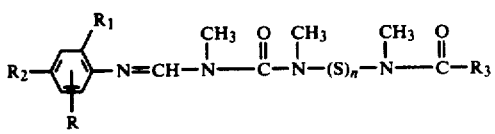

wherein:

n is 1 or 2;

R is hydrogen, halogen or alkyl;

$R_1$ and $R_2$ are individually halogen, alkyl, trihaloalkyl or di- or trihaloalkoxy; provided that the total number of carbon atoms in any one of R, $R_1$ or $R_2$ may not exceed four;

$R_3$ is 1-naphthoxy, tetrahydronaphthoxy, dihydrobenzofuranoxy, benzodioxalanoxy, or benzothienoxy, any of which may be unsubstituted or substituted with one or more alkyl substituents provided that the total number of aliphatic carbon atoms in $R_3$ does not exceed twelve.

63. A method in accordance with claim 62 wherein $R_3$ is dihydrobenzofuranoxy, unsubstituted or substituted with one or more alkyl substituents.

64. A method of controlling insects, mites and nematodes which comprises subjecting them to an insecticidally, miticidally or nematocidally effective amount of a compound of the formula:

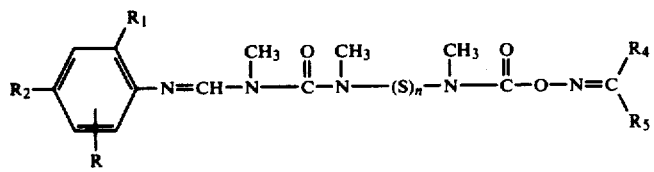

wherein:

n is 1 or 2;

R is hydrogen, halogen or alkyl;

$R_1$ and $R_2$ are individually halogen, alkyl, trihaloalky or di- or trihaloalkoxy; provided that the total number of carbon atoms in any one of R, $R_1$ or $R_2$ may not exceed four;

$R_4$ is chloro, alkyl, alkylthio, cyanoalkylthio, cyano or hydrogen;

$R_5$ is alkyl, alkylthio, alkoxycarbonyl, aminocarbonyl; alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, phenyl or hydrogen said phenyl being unsubstituted or substituted with one or more alkyl, chloro or fluoro substituents in any combination; provided that $R_4$ and $R_5$ are not both hydrogen; and provided further that the total number of aliphatic carbon atoms in $R_4$ and $R_5$ together does not exceed twelve.

65. A method in accordance with claim 64 wherein $R_4$ is alkyl and $R_5$ is alkylthio.

66. A method for controlling insects, mites and nematodes which comprises subjecting them to an insecticidally, miticidally or nematocidally effective amount of a compound of the formula:

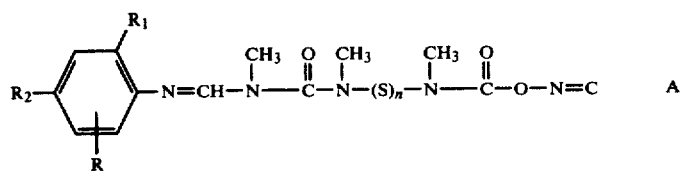

wherein:

n is 1 or 2;

R is hydrogen, halogen or alkyl;

$R_1$ and $R_2$ are individually halogen, alkyl, trihaloalkyl or di- or trihaloalkoxy; provided that the total number of carbon atoms in any one of R, $R_1$ or $R_2$ does not exceed four;

A is a divalent chain having from 2 to 24 aliphatic carbon atoms completing a 2-oximino-1,4-dithiane, 2-oximino-1,3-dithiane, 4-oximino-1,3-dithiolane, 2-oximino-1,4-dioxane, 2-oximino-tetrahydro-1,4-thiazine-3-one, 2-oximino-1,3-dithiolane, 2-imino-4-oximino-1,3-dithiolane, 3-oximinothiophane, 2-oximinothiophane, 2-oximino-tetrahydro-1,4-oxathiane, 4-oximino-1,3-oxathiolane, 2-oximinothiazolidin-3-one, 2-oximino-1,3-thiazolidin-4-one or 2-oximinotetrahydro-1,4-thiazin-5-one ring structure, all of which may be unsubstituted or substituted with one or more alkyl substituents.

67. A method of controlling insects, mites and nematodes which comprises subjecting them to an insecticidally, miticidally or nematocidally effective amount of 1-[7-(2,3-Dihydro-2,2-dimethylbenzofuranyloxy)]-7-(4-chloro-2-methylphenylimino)-2,4,6-triaza-2,4,6-trimethyl-3-thia-1,5-dioxoheptane.

68. A method of controlling insects, mites and nematodes which comprises subjecting them to an insecticidally, miticidally or nematocidally effective amount of 1-(4-Chloro-2-methylphenylimino)-2,4,6,9-tetraaza-2,4,6,10-tetramethyl-8-oxa-5,11-dithia-3,7-dioxododeca-9-ene.

* * * * *